US012558450B2

(12) United States Patent
Chao

(10) Patent No.: US 12,558,450 B2
(45) Date of Patent: Feb. 24, 2026

(54) STRUCTURE OF AN AIRFLOW PUMP AROMA DIFFUSER

(71) Applicants:Hsuan-Yu Chao, Taipei (TW);
Mei-Mei Tsai, Taipei (TW)

(72) Inventor: Hsuan-Yu Chao, Taipei (TW)

( * ) Notice: Subject to any disclaimer, the term of this patent is extended or adjusted under 35 U.S.C. 154(b) by 378 days.

(21) Appl. No.: 18/501,704

(22) Filed: Nov. 3, 2023

(65) Prior Publication Data

US 2024/0408263 A1     Dec. 12, 2024

(30) Foreign Application Priority Data

Jun. 12, 2023     (CN) ......................... 202321487684.3

(51) Int. Cl.
*A61L 9/14*          (2006.01)
(52) U.S. Cl.
CPC ........... *A61L 9/14* (2013.01); *A61L 2209/134* (2013.01); *A61L 2209/135* (2013.01)
(58) Field of Classification Search
CPC ....................................................... A61L 9/14
See application file for complete search history.

(56) References Cited

U.S. PATENT DOCUMENTS 7,878,418 B2     2/2011  Sevy
7,930,068 B2     4/2011  Robert et al.

| | | |
|---|---|---|
| 10,507,258 B2 | 12/2019 | Sevy |
| 11,541,143 B2 | 1/2023 | Sevy |
| 11,666,678 B2 | 6/2023 | Sevy |
| 2010/0084484 A1* | 4/2010 | Sevy .................... A61M 11/001 |
| | | 239/340 |
| 2016/0000959 A1* | 1/2016 | Sevy ......................... A61L 9/14 |
| | | 422/4 |
| 2019/0105615 A1 | 4/2019 | Ansley et al. |
| 2020/0254131 A1* | 8/2020 | Sevy ......................... A61L 9/14 |

FOREIGN PATENT DOCUMENTS

CN          205613606     * 10/2016

* cited by examiner

*Primary Examiner* — Donald R Spamer

(57)          ABSTRACT

An improved structure of an air pump aroma diffuser, comprising a main frame with a circuit board therein which is connected to a motor pump by way of a power supply, and a spray component, wherein the main frame is configured with the motor pump on one side thereof and an inner cavity on the other side thereof to allow the spray component to move in and out, so that the spray component is assembled into the inner cavity from top to bottom; By way of this overall effective combination, the circuit board controls the motor pump to drive the spray component, which can provide different manners as spray output effect and make the spray component easy to press to remove and replace the essential oil bottle. At the same time, it has the advantages of anti-dumping and leakage and operation shock absorption and low noise.

6 Claims, 7 Drawing Sheets

10

STRUCTURE OF AN AIRFLOW PUMP AROMA DIFFUSER

BACKGROUND OF THE INVENTION

Field of the Invention

The present invention relates to the technical field of air purification and aroma diffuser, in particular an improved structure of an airflow pump aroma diffuser.

The Prior Arts

In recent years, the medicalized beauty industries have developed rapidly, and people have paid more and more attention to beauty care and medical health care. The industry has actively developed and designed various aroma diffuser structures, which are used to atomize plant aromatic liquids so that the human body can easily inhale them for aromatherapy.

A common aroma diffuser is known to mainly comprises a base with an air supply motor pump inside. A diffuser bottle is connected to the base, and a special air blowing nozzle and its corresponding straw are provided in the bottle. When the motor pump is started to supply air, the essential oil can be sucked up and atomized by siphoning, so that the aroma of the essential oil can spread quickly and evenly in the air. It lasts for a long time that is very popular among aromatherapy practitioners.

However, most of the known diffusers have an open outlet at the top of the diffuser bottle. Although the atomized aroma can be discharged directly, the structural design is not perfect. In case of accidental collision and overturning, essential oil leakage may occur and the overall shockproof and airtight sound insulation effect is poor. It is easy to vibrate, make noise and disturb the peace of life when used. In addition, the size of the fragrance mist particles released is different when it is used, which often makes the ground near the main frame wet and easily attracts dirt, causing trouble in cleaning.

More advanced improved designs, such as U.S. Pat. No. 7,878,418B2, provide an integrated essential oil atomizer that discloses an injector and a detachable atomizer that is directly connected to the storage and the supporting surface of the pump.

U.S. Pat. No. 7,930,068B2 provides a system and method for controlling the operation of a liquid expansion device. It has been disclosed that an ink cartridge holding liquid is located in a liquid diffuser.

US 20190105615A1 provides an air treatment system is provided which includes an appliance and a replaceable cartridge installable therein. The replaceable cartridge contains a liquid compound to be aerosolized and has a cartridge outlet through which the aerosolized compound is discharged during operation. A pump is provided to supply air to the replaceable cartridge to generate the aerosolized compound from the liquid compound contained in the replaceable cartridge, and a controller is provided for controlling the pump to supply the air to the replaceable cartridge to generate and discharge the aerosolized compound from the appliance. The appliance may further include a lift mechanism to assist in receiving the cartridge and moving the cartridge from a loading position to an operational position.

U.S. Pat. No. 10,507,258B2, U.S. Pat. No. 11,541,143B2, and U.S. Pat. No. 11,666,678B2, these three applications are simple integrated designs based on the same concept of the foregoing patent applications. By integrating the entire diffuser into the form of a threaded cap, the bottle becomes more compact and suitable for operation as a liquid reservoir. The motor and pump system are integrated into a package that fits within the housing, and the entire reservoir and diffuser system is then accommodated in a silo next to the pump and motor.

However, the structural designs of U.S. Pat. No. 10,507, 258 B2, U.S. Pat. No. 11,541,143 B2, and U.S. Pat. No. 11,666,678B2 are still not perfect, and their overall components are too many and too complex. Especially as shown in FIG. 3, parts 42, 66, 72a, 72b, and 60 are not conducive to mold manufacturing and assembled with production. Moreover, as shown in FIGS. 1 and 5, the diffuser 12 and the reservoir 14 are installed in the base 16 during application.

Due to the lack of good docking design, the overall combination cannot be completely flat placement, and there will be obvious section protrudes above the diffuser 12, which limits the appearance of the product and prevents it from being truly flat and beautiful.

SUMMARY OF THE INVENTION

In view of this, the main purpose of the present invention is to provide an improved structure of an air pump aroma diffuser, which comprises: a main frame, which is configured with a motor pump connected to the power supply of the circuit board, and a spray component, wherein The main frame has a cylindrical shell, a base frame is configured at lower position of the shell, and an upper cover is configured at higher position of the shell, wherein an assembly hole and a plurality of buttons are configured on a surface of the upper cover.

An internal framework is configured at higher position of the main frame, the circuit board is located on the internal framework, the motor pump is located at one side of a lower position under the internal framework, and an inner cavity is located at the other side of the lower position under the internal framework, the assembly hole passes through and is connected with a higher position of the internal framework to allow the spray component to move in and out, so that the spray component is assembled into the inner cavity from top to bottom.

The spray component is composed of an atomization diffusion tip, an essential oil bottle and a bottom sleeve which are interconnected with each other, an assembly convex portion is configured under the bottom sleeve, a push locking switch and a spring are correspondingly configured in a bottom hole of the inner cavity.

The air inlet on a side of the atomization diffusion tip, which is corresponding to a side sleeve hole that is configured by the inner cavity, the motor pump is connected through an inverted L-shaped plug-in connecter.

In a preferred embodiment, wherein the main frame is a stand-up type, an USB plug-in part is configured on a side of the shell, which is connected to a battery holder and the circuit board for power supply.

In a preferred embodiment, wherein the main frame is of a wall-plug type, a plug is configured on a side of the shell, which is connected to a battery holder and the circuit board for power supply.

By way of this overall effective combination, the circuit board controls the motor pump to drive the spray component, which can provide different manners as spray output effect and make the spray component easy to press to remove and replace the essential oil bottle. At the same time, it has the advantages of anti-dumping and leakage and operation shock absorption and low noise.

Figure 1:
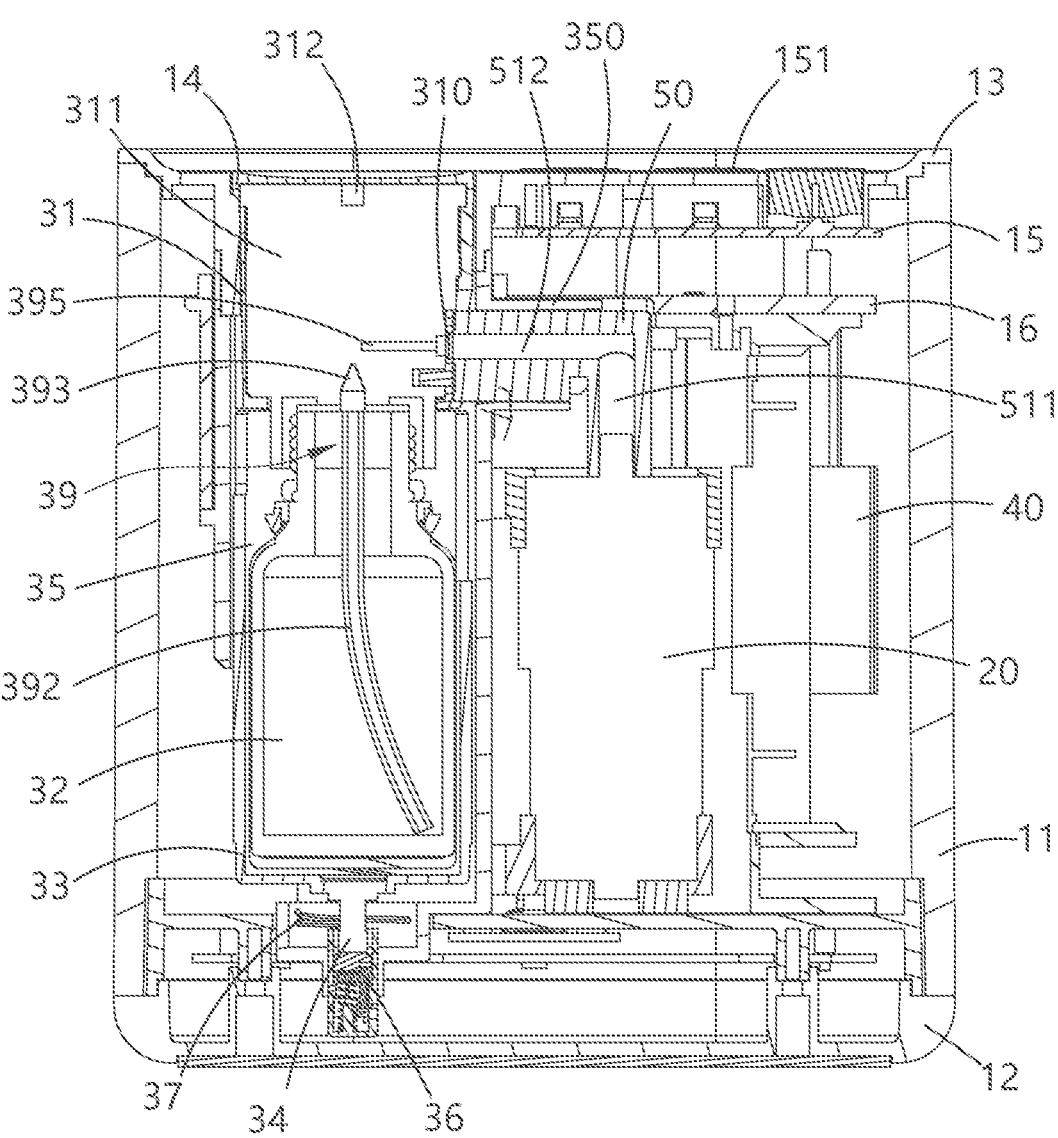
FIG. 1 is a combined cross-sectional view of the present invention.

There are representative symbols shown in foregoing figures. Wherein, main frame 10; shell 11; base frame 12; upper cover 13; operating panel 130; plug hole 131; assembly hole 14; circuit board 15; button 151; internal framework 16; cylindrical vent 161; motor pump 20; fixed ring 21: fixed arm 212; shock absorbing pad 22; spray component 30; atomization diffusion tip 31; air inlet 310; atomization cavity 311; fog outlet 312; essential oil bottle 32; bottom sleeve 33; assembly convex portion 34; inner cavity 35; side sleeve hole 350; protruding cylinder 352; push locking switch 36; spring 37; siphon atomization structure 39; siphon pipe 392; atomized head portion 393; inlet head portion 395; airflow pipeline 396; airflow baffle 397; nozzle 398; connecting pipe 399; battery holder 40; USB plug-in part 41; plug 42; plug-in connecter 50; first connecting portion 501; second connecting portion 502; first pipe 511; second pipe 512.

DETAILED DESCRIPTION OF PREFERRED EMBODIMENTS

For the convenience of understanding the content of the present invention and the effects that can be achieved, specific embodiments are listed in conjunction with the drawings, and the detailed description is as follows: As shown in FIGS. 1 to 5, the present invention provides an improved structure of an air pump aroma diffuser, which comprises: a main frame 10 with a circuit board 15 therein which is connected to a motor pump 20 by way of a power supply, and a spray component 30, wherein The main frame 10 has a cylindrical shell 11, a base frame 12 is configured at lower position of the shell 11, and an upper cover 13 is configured at higher position of the shell 11, wherein an assembly hole 14 and a plurality of buttons 151 are configured on a surface of the upper cover 13.

An internal framework 16 is configured at higher position of the main frame 10, the circuit board 15 is located on the internal framework 16, the motor pump 20 is located at one side of a lower position under the internal framework 16, and an inner cavity 35 is located at the other side of the lower position under the internal framework 16, the assembly hole 14 passes through and is connected with a higher position of the internal framework 16 to allow the spray component 30 to move in and out, so that the spray component 30 is assembled into the inner cavity 35 from top to bottom.

The spray component 30 is composed of an atomization diffusion tip 31, an essential oil bottle 32 and a bottom sleeve 33 which are interconnected with each other, an assembly convex portion 34 is configured under the bottom sleeve 33, a push locking switch 36 and a spring 37 are correspondingly configured in a bottom hole of the inner cavity 35.

The air inlet 310 on a side of the atomization diffusion tip 311, which is corresponding to a side sleeve hole 350 that is configured by the inner cavity 35, the motor pump 20 is connected through an inverted L-shaped plug-in connecter 50.

In a preferred embodiment, wherein the plug-in connecter 50 is made of silicone and comprises an integrally formed a first connecting portion 501 and a second connecting portion 502, wherein the first connecting portion 501 is configured with a first pipe 511 which is connected to the motor pump 20, the second connecting portion 502 is configured with a second pipe 512 which is configured with the side sleeve hole 350, so that the motor pump 20 is connected to the inner cavity 35.

In a preferred embodiment, wherein a battery holder 40 is further configured among an outer side of the motor pump 20 and an inner wall space of the shell 11, which is connected to the circuit board 15 for power supply.

Figure 2:
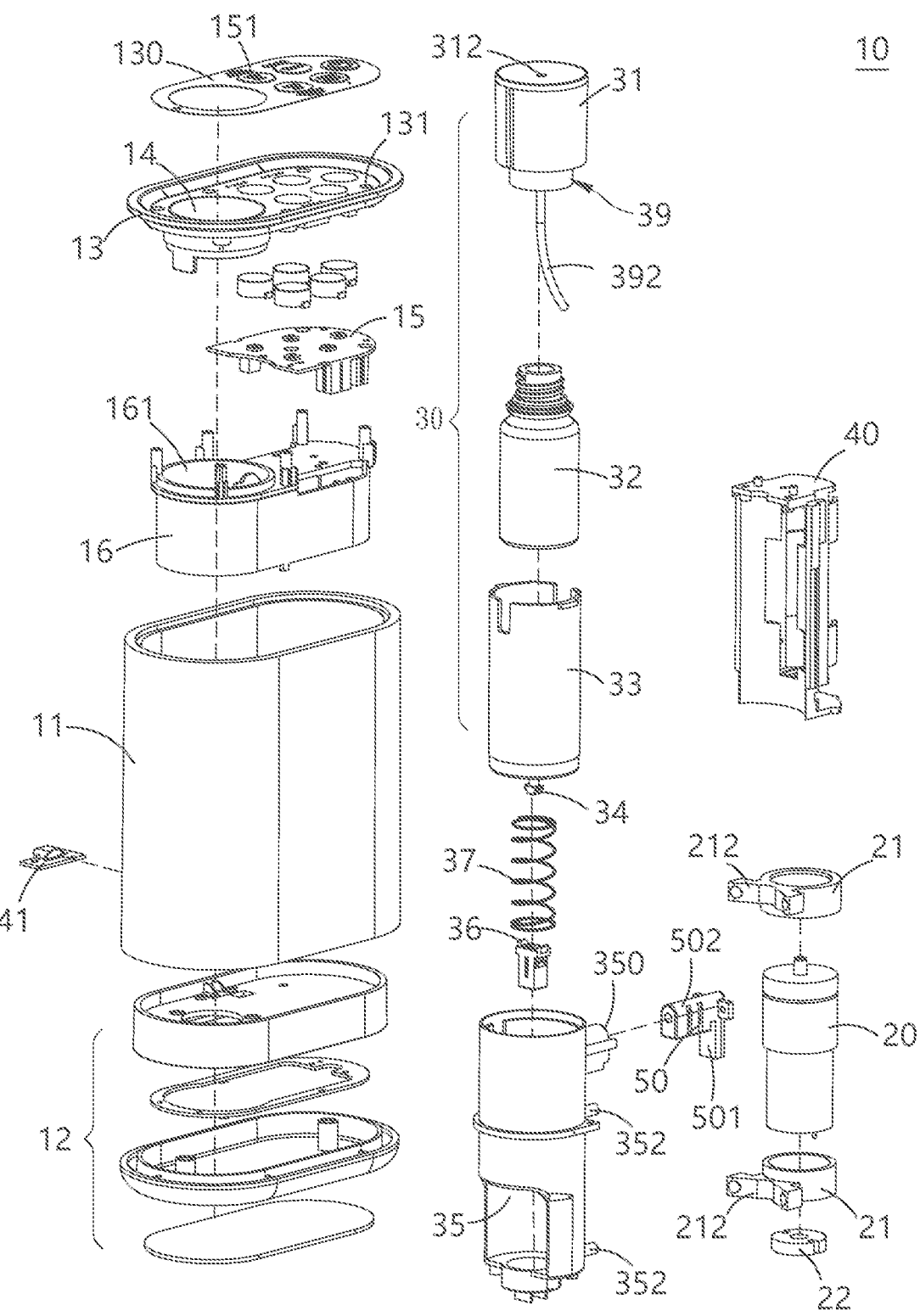
FIG. 2 is a three-dimensional exploded view of the stand-up diffuser of the present invention.
Figures 3A, 3B:
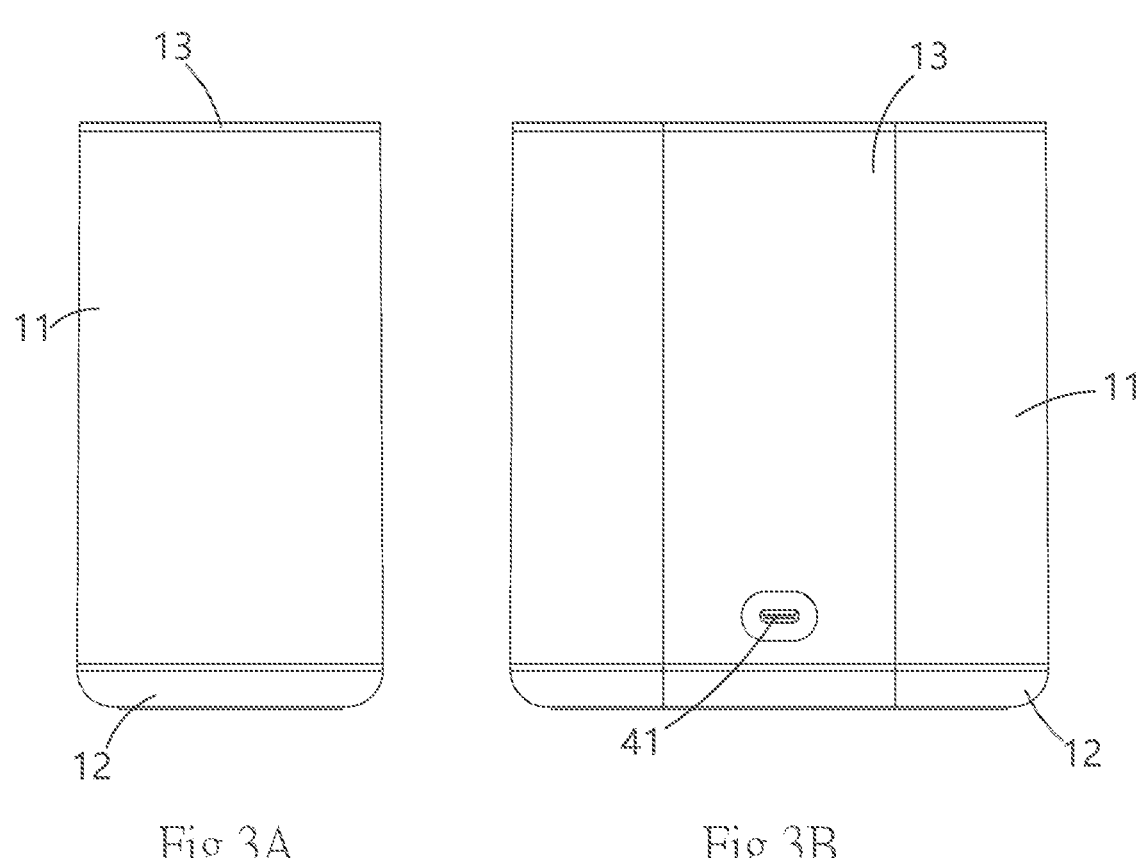
FIGS. 3A to 3C are three-side views of the stand-up diffuser of the present invention.
Figure 3C:
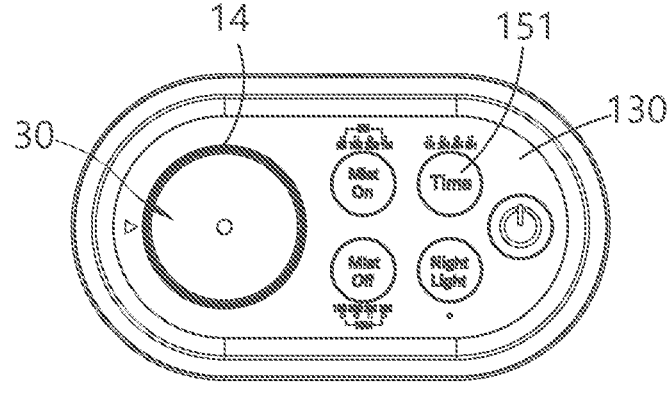

In a preferred embodiment, as shown in FIG. 2 to FIG. 3C, wherein the main frame 10 is a stand-up type, an USB plug-in part 41 is configured on a side of the shell 11, which is connected to a battery holder 40 and the circuit board 15 for power supply.

Figures 4A, 4B:
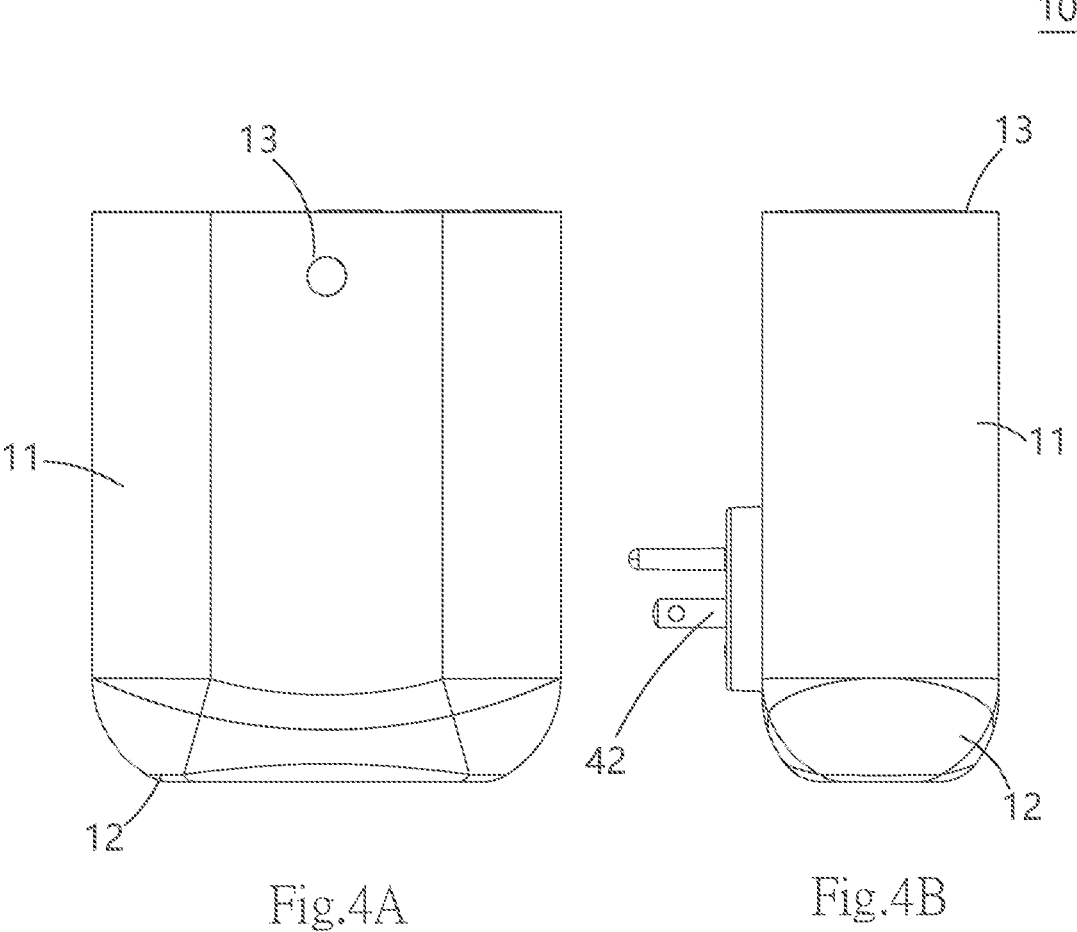
FIGS. 4A to 4C are three-side views of the wall-plugged diffuser of the present invention.
Figure 4C:
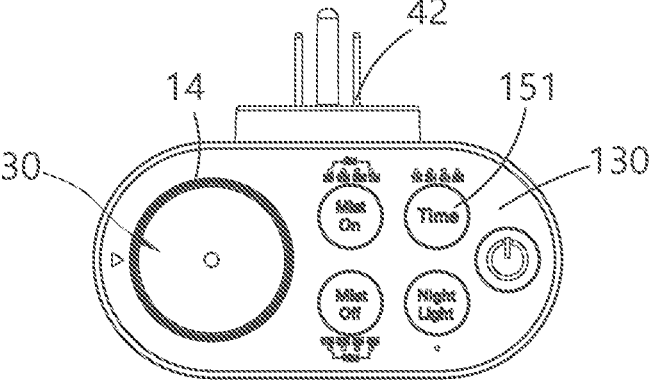
Figure 5:
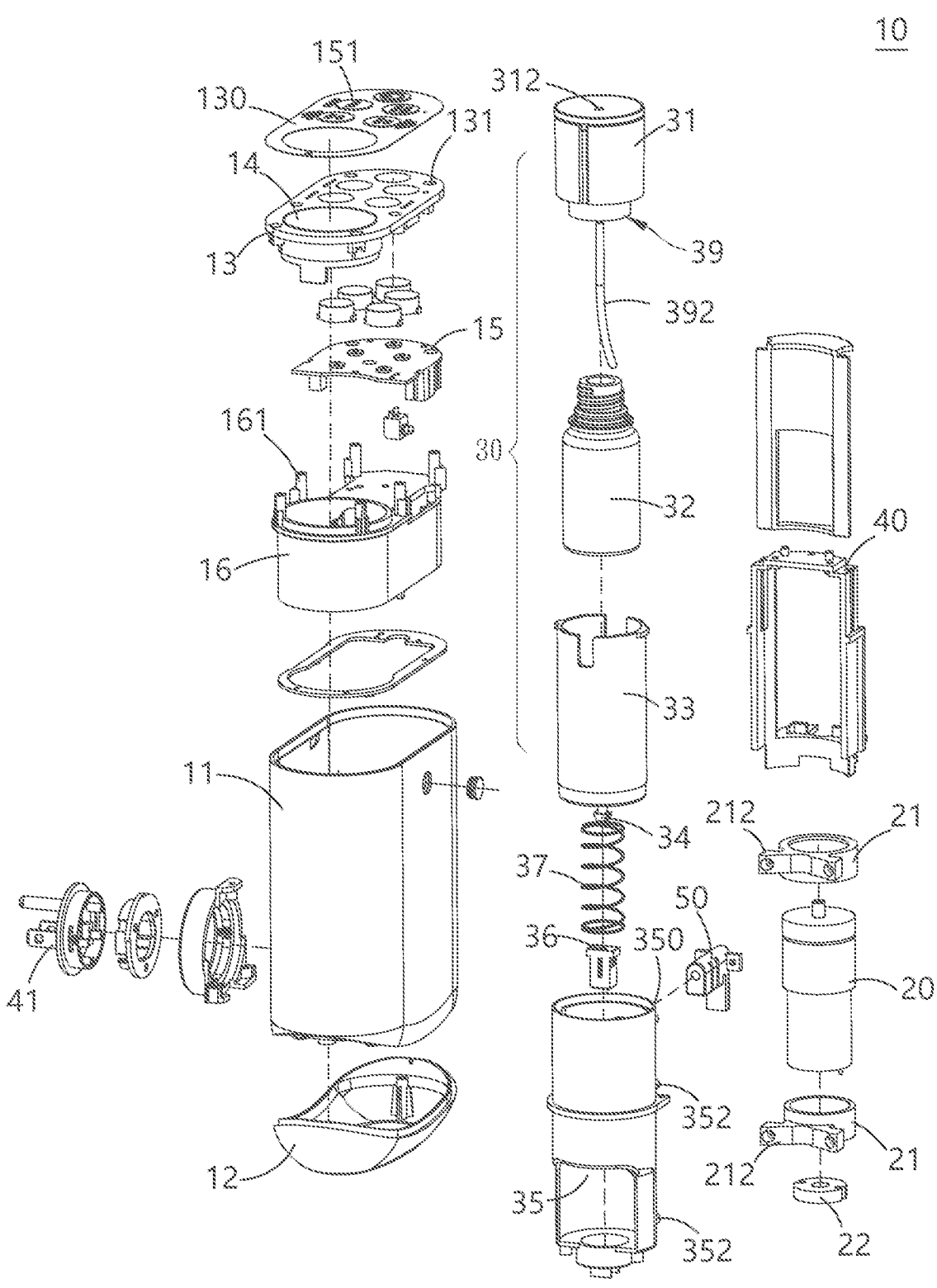
FIG. 5 is a three-dimensional exploded view of the wall-plugged diffuser of the present invention.

In a preferred embodiment, as shown in FIG. 4A to FIG. 5, wherein the main frame 10 is of a wall-plug type, a plug 42 is configured on a side of the shell 11, which is connected to a battery holder 40 and the circuit board 15 for power supply.

By way of this overall effective combination, the circuit board 15 controls the motor pump 20 to drive the spray component 30, which can provide different manners as spray output effect and make the spray component 30 easy to press to remove and replace the essential oil bottle 32. At the same time, it has the advantages of anti-dumping and leakage and operation shock absorption and low noise.

In a preferred embodiment, as shown in FIG. 2, FIG. 5, wherein the motor pump 20 is configured with a fixed ring 21 on an upper side thereof and another fixed ring 21 on a lower side thereof, a shock absorbing pad 22 is configured on a bottom of the motor pump 20, wherein a side of each fixed ring 21 has a V-shaped fixed arm 212 with a connection hole, two spacing protruding cylinders 352 are respectively separated to configure on a upper side and a lower side of a outer wall of the inner cavity 35 for connection and fixation. But in fact, it is not limited to foregoing description.

In a preferred embodiment, wherein the internal framework 16 is configured with a plurality of cylindrical vents 161 at intervals around the internal framework 16, the upper cover 13 is formed the shape of a shallow plate, a surrounding of the upper cover 13 is configured with plug holes 131 correspondingly for combination locking, an operation panel 130 is further configured on the upper cover 13.

In a preferred embodiment, as shown in FIG. 1, wherein the atomization diffusion tip 31 comprises an atomization cavity 311 with a fog outlet 312 thereon, a siphon atomization structure 39 is configured at a bottom of the atomization diffusion tip 31, an inlet head portion 395 is connected to an air inlet 310 through a side of the atomization diffusion tip 31, the inner cavity 35 is connected with the siphon atomization structure 39, the siphon atomization structure 39 comprises a siphon pipe 392 that passes through the atomization cavity 311, one end of the siphon atomization structure 39 is inserted into the essential oil bottle 32, the other end of the siphon atomization structure 39 is located in the atomization cavity 35 with an atomized head portion 393.

Figure 6:
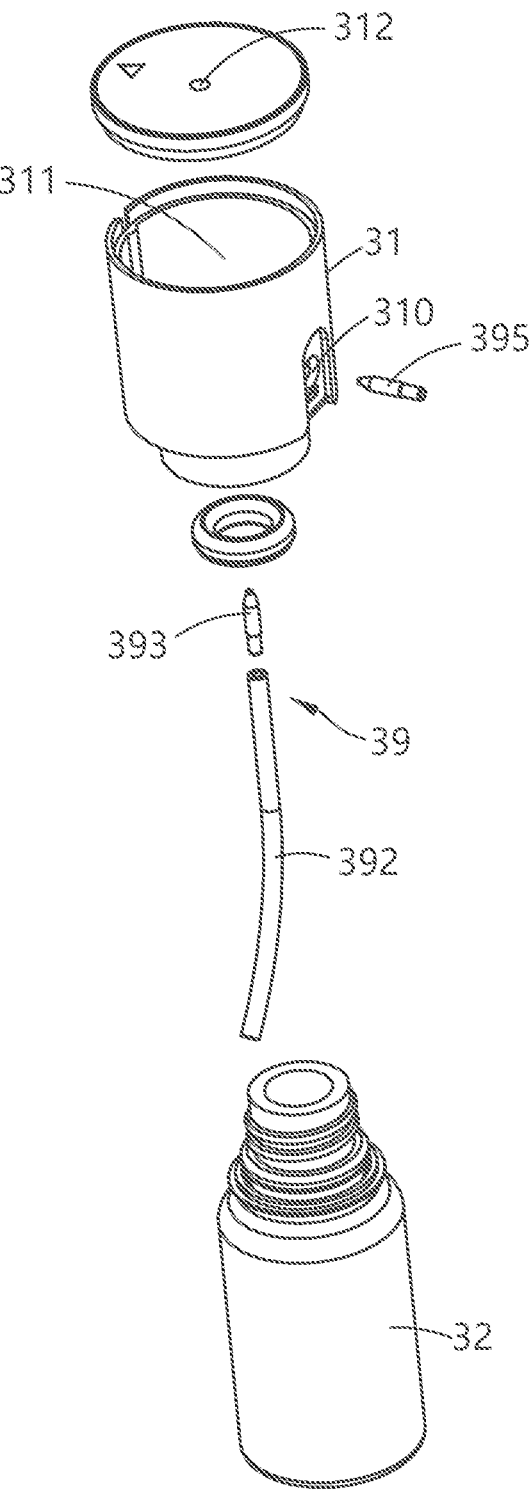
FIG. 6 is a three-dimensional exploded view of the atomization diffusion tip of the present invention.
Figure 7:
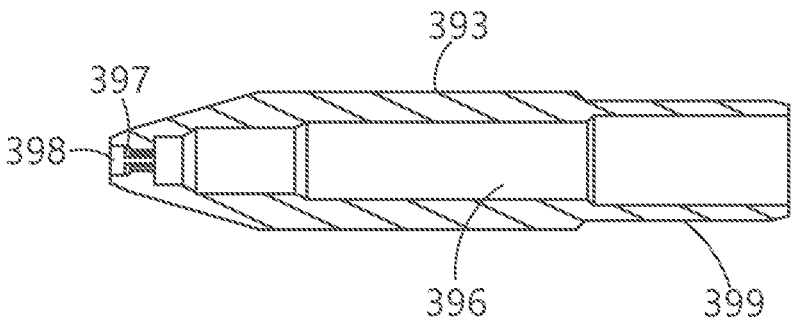
FIG. 7 is a schematic cross-sectional view of the atomized head portion of the present invention.
Figure 8:
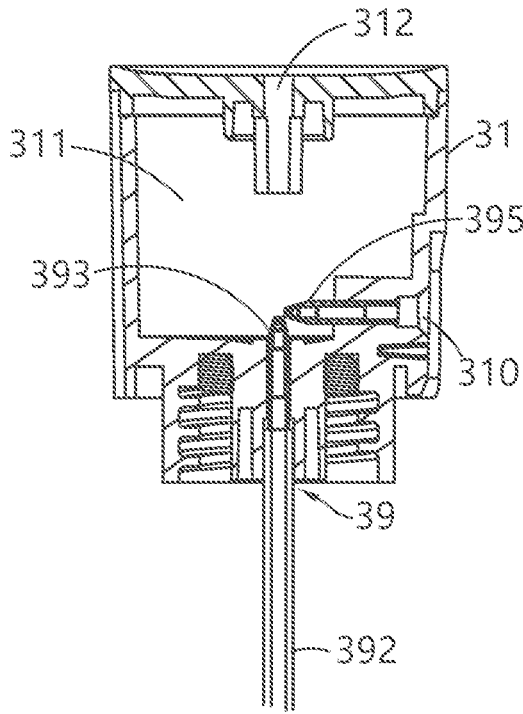
FIG. 8 is an assembled cross-sectional view of the atomization diffusion tip of the present invention.

In a preferred embodiment, as shown in FIG. 6 to FIG. 8, wherein the atomized head portion 393 and the inlet head portion 395 are further configured as mouth tubes with the same shape, which are made of integrally formed metal, each said mouth tube is configured with a reduced diameter connecting pipe 399 at the rear of said mouth tube and a nozzle 398 which is bullet-shaped blunt tip at the front of said mouth tube, the nozzle 398 is configured with airflow baffles 397 which has intervals distributed in an inner diameter of the nozzle 398, a multi-stage airflow pipeline 396 is configured in said mouth tube. The angle between the atomized head portion 393 and the inlet head portion 395 is less than 90°. Since the inlet head portion 395 and the atomized head portion 393 have the same shape, they will not be described again.

In a preferred embodiment, the atomized head portion 393 and the inlet head portion 395 can be made of metal in one piece. The metal atomized head portion 393 and the inlet head portion 395 can be conveniently plugged, connected, assembled at a fixed point. In place, the fixing effect of the combined structure is better. The solid metal can reduce the noise caused by swinging in the wind. The biggest advantage is that the metal atomized head portion 393 and the inlet head portion 395 can maintain an appropriate distance that has been tested by actuarial experiments to comply with the Bernoulli principle atomization effect, reach the best condition, so that the essential oil is completely atomized in the atomization cavity 311, so the spray effect can be better, and at the same time, it can further effectively reduce the noise and reduce the sound of outgassing.

Please refer to FIGS. 1 to 8. By adopting the foregoing technical solution, the present invention allows the spray component 30 to be inserted into the main frame 10 and fixedly connected to form a more solid integrated combination. The spray component 30 and the essential oil bottle 32 are detachably connected. When replacing the essential oil bottle 32, only need to take out the entire spray component 30 to remove the essential oil bottle 32 for replacement. The structure is simple and effective, and the operation is very convenient and fast.

When replacing, just press the atomization diffusion tip 31 and release the push locking switch 36 at the bottom of the inner cavity 35, so that the assembly convex portion 34 of the bottom sleeve 33 can be detached, and the spray component 30 can be ejected and supported by the spring 37. so that the disassembled essential oil bottle 32 can be removed and replaced, and then the whole assembled module is put back into the inner chamber 35, the assembly convex portion 34 of the bottom sleeve 33 is pressed to the bottom, so that the push locking switch 36 at the bottom of the inner cavity 35 is is closed and locked, so that the replacement of the essential oil bottle 32 can be easily completed.

During use, the motor pump 20 is connected with the inner cavity 35, and the inner cavity 35 is connected and conducted with the atomization cavity 311 through the air inlet 310. When the motor pump 20 is started, the motor pump 20 continues to inject air into the inner cavity 35. The pressurized air in the inner cavity 35 can enter the atomization cavity 311 through the air inlet 310. Through the siphon atomization structure 39, the fragrance liquid obtains a good atomization effect and is discharged to the outside through the fog outlet 312. In use, it has significant advantages such as wide atomization range (atomizably extremely high viscosity essential oils), good visibility of the atomized gas state, small particles, fast diffusion, improvement of fragrance mist splashing on the ground, and improvement of oil leakage.

The structure of the present invention is tightly assembled and basically has the function of blocking sound transmission. Moreover, the motor pump 20 is configured with a fixed ring 21 on the upper and lower sides thereof, which can effectively improve the stability and thereby reduce part of the noise. In addition, there is a shock absorbing pad 22 at the bottom, and the plug-in connecter 50 made of silicone has good elasticity and can greatly buffer the vibration generated by the motor pump 20, so it can achieve good anti-vibration and noise reduction to be practical effect.

To sum up, the present invention is novel and practical and fully meets the patent requirements, and the present invention application is proposed. However, the foregoing descriptions are only preferred embodiments of the present invention, should not be used to limit the scope of the present invention. Therefore, any equivalent changes and modifications made in accordance with the claims and description of the present invention, all of which should fall within the scope of the present invention patent.

What is claimed is:

1. An improved structure of an air pump aroma diffuser, comprising: a main frame with a circuit board therein which is connected to a motor pump by way of a power supply, and a spray component, wherein the main frame has a cylindrical shell, a base frame is configured at lower position of the shell, and an upper cover is configured at higher position of the shell, wherein an assembly hole and a plurality of buttons are configured on a surface of the upper cover;

an internal framework is configured at higher position of the main frame, the circuit board is located on the internal framework, the motor pump is located at one side of a lower position under the internal framework, and an inner cavity is located at the other side of the lower position under the internal framework, the assembly hole passes through and is connected with a higher position of the internal framework to allow the spray component to move in and out, so that the spray component is assembled into the inner cavity from top to bottom;

the spray component is composed of an atomization diffusion tip, an essential oil bottle and a bottom sleeve which are interconnected with each other, an assembly convex portion is configured under the bottom sleeve, a push locking switch and a spring are correspondingly configured in a bottom hole of the inner cavity;

wherein the atomization diffusion tip comprises an atomization cavity with a fog outlet thereon, a siphon atomization structure is configured at a bottom of the atomization diffusion tip, an inlet head portion is connected to an air inlet through a side of the atomization diffusion tip, the inner cavity is connected with the siphon atomization structure, the siphon atomization structure comprises a siphon pipe that passes through the atomization cavity, one end of the siphon atomization structure is inserted into the essential oil bottle, the other end of the siphon atomization structure is located in the atomization cavity with an atomized head portion, the angle between the atomized head portion and the inlet head portion is less than 90°;

wherein the atomized head portion and the inlet head portion are further configured as mouth tubes with the same shape, which are made of integrally formed metal, each said mouth tube is configured with a reduced diameter connecting pipe at the rear of said mouth tube and a nozzle which is bullet-shaped blunt tip at the front of said mouth tube, the nozzle is configured with airflow baffles which has intervals distributed in an inner diameter of the nozzle, a multi-stage airflow pipeline is configured in said mouth tube; and the air inlet on a side of the atomization diffusion tip, which is corresponding to a side sleeve hole that is configured by the inner cavity, the motor pump is connected through an inverted L-shaped plug-in connecter;

wherein the plug-in connecter is made of silicone and comprises an integrally formed a first connecting portion and a second connecting portion, wherein the first connecting portion is configured with a first pipe which is connected to the motor pump, the second connecting portion is configured with a second pipe which is configured with the side sleeve hole, so that the motor pump is connected to the inner cavity.

2. The improved structure of the air pump aroma diffuser as claimed in claim 1, wherein the motor pump is configured with a fixed ring on an upper side thereof and another fixed ring on a lower side thereof, a shock absorbing pad is configured on a bottom of the motor pump, wherein a side of each fixed ring has a V-shaped fixed arm with a connection hole, two spacing protruding cylinders are respectively separated to configure on a upper side and a lower side of a outer wall of the inner cavity for connection and fixation.

3. The improved structure of the air pump aroma diffuser as claimed in claim 1, wherein the internal framework is configured with a plurality of cylindrical vents at intervals around the internal framework, the upper cover is formed the shape of a shallow plate, a surrounding of the upper cover is configured with plug holes correspondingly for combination locking, an operation panel is further configured on the upper cover.

4. The improved structure of the air pump aroma diffuser as claimed in claim 1, wherein a battery holder is further configured among an outer side of the motor pump and an inner wall space of the shell, which is connected to the circuit board for power supply.

5. The improved structure of the air pump aroma diffuser as claimed in claim 1, wherein the main frame is a stand-up type, an USB plug-in part is configured on a side of the shell, which is connected to a battery holder and the circuit board for power supply.

6. The improved structure of the air pump aroma diffuser as claimed in claim 1, wherein the main frame is of a wall-plug type, a plug is configured on a side of the shell, which is connected to a battery holder and the circuit board for power supply.

* * * * *